United States Patent
Almberg et al.

(10) Patent No.: US 8,444,619 B2
(45) Date of Patent: *May 21, 2013

(54) BELTED ABSORBENT ARTICLE

(75) Inventors: Christian Almberg, Mölnlycke (SE); Lucas Bäck, Goteborg (SE)

(73) Assignee: SCA Hygiene Products AB, Göteborg (SE)

( * ) Notice: Subject to any disclaimer, the term of this patent is extended or adjusted under 35 U.S.C. 154(b) by 1431 days.

This patent is subject to a terminal disclaimer.

(21) Appl. No.: 10/684,585

(22) Filed: Oct. 15, 2003

(65) Prior Publication Data

US 2004/0138640 A1    Jul. 15, 2004

Related U.S. Application Data

(63) Continuation of application No. 09/902,656, filed on Jul. 12, 2001, now Pat. No. 6,726,670.

(60) Provisional application No. 60/218,050, filed on Jul. 13, 2000.

(30) Foreign Application Priority Data

Jul. 13, 2000 (SE) .................................. 00002660

(51) Int. Cl.
*A61F 13/15* (2006.01)

(52) U.S. Cl.
USPC ........ 604/392; 604/394; 604/385.3; 604/391; 604/390; 604/402; 604/385.11

(58) Field of Classification Search
USPC .............. 604/392, 394, 385.3, 391, 390, 401, 604/402, 385.11
See application file for complete search history.

(56) References Cited

U.S. PATENT DOCUMENTS

| 4,964,860 A | 10/1990 | Gipson et al. |
| 5,300,055 A | 4/1994 | Buell |

(Continued)

FOREIGN PATENT DOCUMENTS

| EP | 0 287 388 A2 | 10/1988 |
| EP | 0 336 578 A1 | 10/1989 |

(Continued)

OTHER PUBLICATIONS

Decision to Refuse issued in a corresponding European patent application dated Jul. 10, 2005.

(Continued)

*Primary Examiner* — Jacqueline F. Stephens
(74) *Attorney, Agent, or Firm* — Buchanan Ingersoll & Rooney PC (57) ABSTRACT

A belted absorbent article (10) having an absorbent structure (16) and a pair of opposed belt halves (12, 14) attached to the absorbent structure (16) via a respective joint (50). The joint (50) between each belt half (12, 14) and the absorbent structure (16) is designed such that when each belt half is subjected to a tension force of 35 N acting along the belt half and the direction of applied tension creates an angle ($\alpha$) to the transverse axis (T) of the absorbent structure, the following minimum average release times (t) of each belt half from the absorbent structure are attained:

when $\alpha=10°$, $t \gg 720$ seconds;
when $\alpha=20°$, $t \gg 330$ seconds;
when $\alpha=25°$, $t \gg 240$ seconds;
when $\alpha=30°$, $t \gg 180$ seconds; and
when $\alpha=40°$, $t \gg 75$ seconds.

7 Claims, 10 Drawing Sheets

U.S. PATENT DOCUMENTS

| | | | |
|---|---|---|---|
| 5,496,429 | A | 3/1996 | Hasse et al. |
| 5,509,914 | A | 4/1996 | Osborn, III |
| H1674 | H * | 8/1997 | Ames et al. .................. 604/389 |
| 5,653,704 | A | 8/1997 | Buell et al. |
| 5,706,524 | A | 1/1998 | Herrin et al. |
| 5,904,673 | A | 5/1999 | Roe et al. |
| 5,906,008 | A | 5/1999 | Heki et al. |
| 6,500,163 | B2 | 12/2002 | Rönnberg et al. |
| 6,540,731 | B2 | 4/2003 | Magnussson et al. |
| 6,575,953 | B2 | 6/2003 | Olson |
| 6,582,543 | B1 | 6/2003 | Nilsson et al. |
| 2001/0034511 | A1 | 10/2001 | Hermansson et al. |
| 2002/0091367 | A1 | 7/2002 | Kusibojoska et al. |
| 2002/0099353 | A1 | 7/2002 | Olson |
| 2003/0100878 | A1 * | 5/2003 | Leak et al. .................. 604/386 |

FOREIGN PATENT DOCUMENTS

| | | |
|---|---|---|
| EP | 0 409 307 A2 | 1/1991 |
| EP | 0 418 493 A1 | 3/1991 |
| EP | 0 486 006 A | 5/1992 |
| EP | 0 605 012 A1 | 7/1994 |
| EP | 0 617 941 | 10/1994 |
| EP | 729329 | 3/1999 |
| EP | 1 216 679 A2 | 6/2002 |
| FR | 2 586 558 | 3/1987 |
| FR | 2586558 | 3/1987 |
| GB | 1 200 177 | 7/1970 |
| GB | 2 216 774 A | 10/1989 |
| GB | 2 283 661 A | 5/1995 |
| JP | 60-25701 | 2/1985 |
| JP | 4-75523 | 7/1992 |
| JP | 5-91643 | 12/1992 |
| JP | 7-116192 | 5/1995 |
| JP | 11-019128 | 1/1999 |
| TW | 233473 | 11/1994 |
| WO | 91/08725 | 6/1991 |
| WO | 94/26222 | 11/1994 |
| WO | 94/26224 | 11/1994 |
| WO | 94/26225 | 11/1994 |
| WO | WO 95/13772 | 5/1995 |
| WO | 95/14453 | 6/1995 |
| WO | 97/31605 | 9/1997 |
| WO | 97/33547 | 9/1997 |
| WO | 97/34037 | 9/1997 |
| WO | 98/37847 | 9/1998 |
| WO | 99/21522 | 5/1999 |
| WO | 99/37263 | 7/1999 |
| WO | 99/37263 A1 | 7/1999 |
| WO | 00/27330 | 5/2000 |
| WO | 01/00129 A1 | 1/2001 |
| WO | 01/74283 A1 | 10/2001 |
| WO | 02/03901 A1 | 1/2002 |
| WO | 02/05739 A1 | 1/2002 |
| WO | 02/22061 A1 | 3/2002 |
| WO | 02/22062 A1 | 3/2002 |
| WO | 02/22063 A1 | 3/2002 |
| WO | 02/22064 A1 | 3/2002 |
| WO | 02/22065 A1 | 3/2002 |
| WO | 02/24134 A1 | 3/2002 |
| WO | 02/24135 A1 | 3/2002 |
| WO | 02/49567 A1 | 6/2002 |
| WO | 02/49568 A1 | 6/2002 |

OTHER PUBLICATIONS

A Trial Decision issued in corresponding Japanese Patent Application No. 2002-511678, dated Oct. 16, 2007, and translation thereof.
Notice of Opposition issued in corresponding European Patent No. EP 1309302 B, dated Sep. 8, 2008.
Leo Osterheider GmbH—German Abri-Wing leaflet dated Aug. 1999; 2 pages.
English Abri-Wing Brochure dated May 2000; 1 page.
Swedish Abri-Wing Brochure dated Aug. 1999; 2 pages.
Decision of the Technical Board of Appeal issued in corresponding European Patent No. EP 1309302 B, dated Sep. 27, 2006; 9 pages.
Witness statement of Lars Neertoft of Abena International A/S ("Abena") dated Aug. 19, 2008.
Email confirmation from Takamasa Takagi of Koyo Corporation ("Koyo") dated Aug. 11, 2008.
Statistics fro Abri-Wing sales, Aug. 6, 2008.
Invoice dated Aug. 17, 1999.
Invoice dated Oct. 14, 1999.
Invoice dated Oct. 20, 1999.
Invoice dated Dec. 17, 1999.
Invoice dated May 5, 2000.
Invoice dated Jun. 28, 2000.
Invoice dated Aug. 13, 1999.
Invoice dated Oct. 4, 1999.
Invoice dated Oct. 5, 1999.
Invoice dated Oct. 6, 1999.
Invoice dated Nov. 10, 1999.
Brochure for the 2007 version of the Abri-Wing.
Letter dated May 22, 20089—Abena.
Letter dated Jun. 20, 2008—Abena.
Test report from the SP Technical Research Institute of Sweden—dated Jul. 4, 2008.
Photograph of an incontinence article (Abri-Wing, manufactured in 2006) tested by SP.
Photograph of the package containing the incontinence articles (Abri-Wing manufactured in 2006) tested by SP.
Photograph of the SP test rig during testing of an incontinence article (Abri-Wing, manufactured 2006).
Close-up photograph of the clamping device of the SP test rig during testing of an incontinence article (Abri-Wing, manufactured in 2006).
Test report from the SP Technical Research Institute of Sweden—dated Aug. 15, 2008 (Abri-Wing, manufactured in 1999, first test).
Photograph of the SP test rig during testing of an incontinence article (Abri-Wing, manufactured in 1999).
Test report from the SP Technical Research Institute of Sweden—dated Aug. 14, 2008 (Abri-Wing, manufactured in 1999, second test).
ASTM d 3654 (1982) American Society for Testing and Materials—"Standard Test Method for Holding Power of Pressure-Sensitive Tapes".

* cited by examiner

BELTED ABSORBENT ARTICLE

CROSS-REFERENCE TO RELATED APPLICATIONS

The present application claims the priority of Swedish Patent Application No. SE 0002660-9, filed in Sweden on Jul. 13, 2000, and claims the benefit of U.S. Provisional Application No. 60/218,050, filed in the United States on Jul. 13, 2000. The contents of Swedish Patent Application No. SE 0002660-9 and U.S. Provisional Application No. 60/218,050 are hereby incorporated herein by reference.

BACKGROUND OF THE INVENTION

1. Technical Field

The present invention relates to a belted absorbent article in the form of a diaper, an adult incontinence garment, and the like, comprising an absorbent structure and a pair of opposed belt halves attached to the absorbent structure at an end region thereof.

2. Discussion of Related Art

Conventional diapers for young children generally comprise an absorbent structure made up of an absorbent core sandwiched between a liquid pervious topsheet and a liquid-impervious backsheet. The absorbent structure has a front panel generally covering the child's abdomen when worn and a rear panel generally covering the child's buttocks. The front and rear panels terminate in front and rear end regions respectively. In order to secure the diaper about the child, the front and rear end regions are provided with cooperating fastening means, for example in the form of a hook-and-loop fastening system or, alternatively, an adhesive tape tab system on the rear end region cooperating with a landing zone on the front end region. To fit the diaper to the child, the child is normally laid down on his/her back, the diaper is inserted under the child such that the rear panel covers the child's buttocks, the front panel is drawn between the child's legs to cover the abdomen and the fastening system is employed to join the longitudinal sides of the respective front and rear end regions together.

Since it is almost exclusively a guardian who changes a child's diaper, the above-described method of securing a diaper to a child is generally fully satisfactory. However, particularly for incontinent adults who are capable of changing their own diapers, such a method of securing an absorbent article about the body is inconvenient, primarily because the act of securing the absorbent article about the adult body is conducted when standing. Thus, it is awkward for the wearer to simultaneously hold the absorbent article to the body in its correct orientation whilst fastening the front and rear end regions to each other.

To at least partially alleviate the above-mentioned inconvenience, belted absorbent articles have been proposed. For example, a belted absorbent article is disclosed in FR-A-2 586 558 in which a one-piece belt is attached to the backsheet of an absorbent structure. The article is secured about the wearer by bringing the article to the rear of the wearer to thereby cover the buttocks, fastening the belt about the waist of the wearer and then drawing the front end region of the absorbent structure between the legs of the wearer and attaching the front end region to fastening means on the belt.

EP-B-0 729 329 discloses a belted absorbent article in which, rather than using a single belt attached to the absorbent structure, two belt halves are employed, with each belt half extending from a respective longitudinal edge of the absorbent structure. An advantage of this construction over that disclosed in FR-A-2 586 558 is that less belt material is needed. However, because two belt halves are employed, the joint between each belt half and the absorbent structure must be capable of withstanding the tension forces to which the belt halves are typically subjected during use.

Particularly in terms of adult incontinence diapers, the size of wearers varies greatly. In order to rationalize production and storage as much as possible, it is preferable to have as few product size variations as possible. This implies, on the other hand, that each product size must be capable of fitting wearers of widely diverging shape and size. As a consequence, the forces to which the belt halves are subjected during use will be, at least to a certain extent, dependent on the size of the wearer. To keep manufacturing costs low, it is of course advantageous to use as little material as possible. Nevertheless, a product must be sufficiently strong to fulfil its intended purpose.

Figure 1:
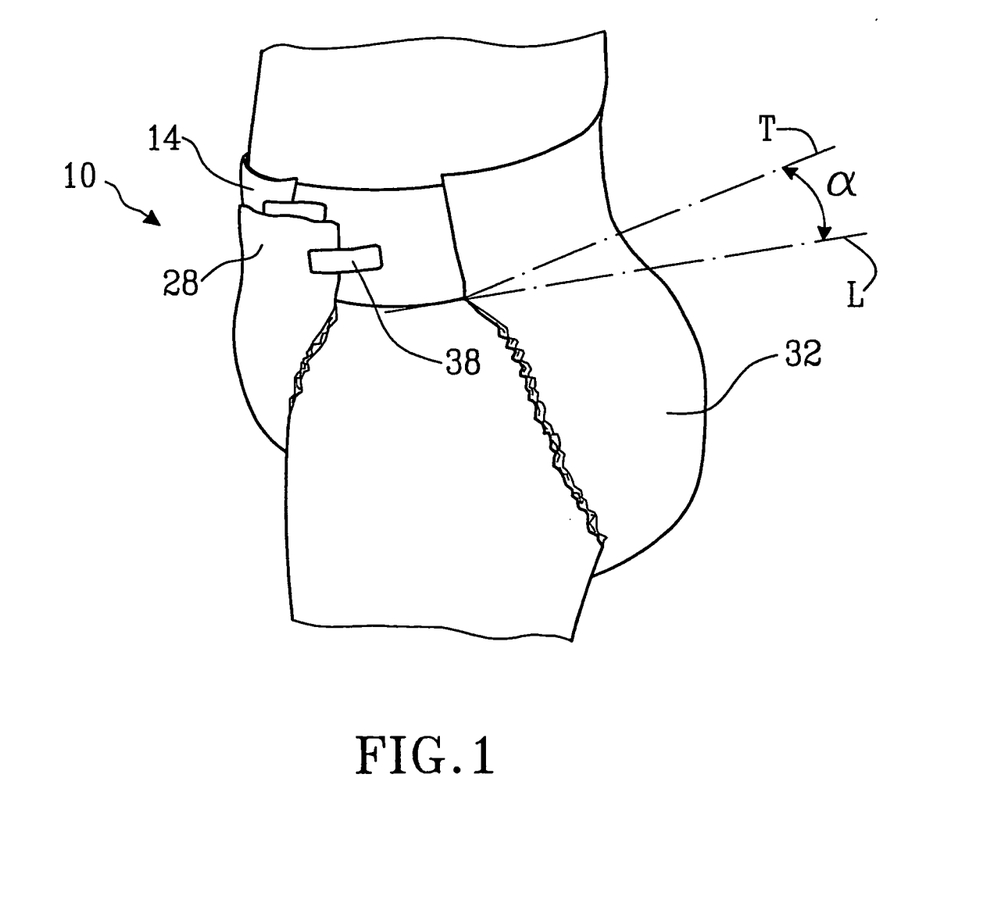
FIG. 1 is a schematic side view of a belted absorbent article secured to a wearer.

As is apparent from FIG. 1, when a belted absorbent article 10 is secured to a wearer, an angle $\alpha$ is created between, in effect, the longitudinal axis L of the belt half and the transverse axis T of the absorbent structure (it being assumed in the illustrated embodiment that the longitudinal edge of the belt half is parallel to the longitudinal axis of the belt half). Depending on the size of the wearer in relation to the size of the article, the value of $\alpha$ will vary. The greater the size of wearer, the greater the value of $\alpha$ will be. As the angle $\alpha$ increases, an increasing shear force is applied to the joint between the belt half and the absorbent structure.

The present applicant has discovered that, in order for a belted absorbent article to function satisfactorily, while still keeping manufacturing costs as low as reasonably possible, the joint between each belt half and the absorbent structure should preferably meet certain minimum requirements depending on the angle $\alpha$.

OBJECTS AND SUMMARY

It is therefore an object of the present invention to provide a belted absorbent article which functions satisfactorily while still keeping manufacturing costs as low as reasonably possible.

This object is achieved by means of the belted absorbent article comprising an absorbent structure extending about a first longitudinal axis, the absorbent structure including a topsheet, a backsheet and an absorbent batt disposed between the topsheet and the backsheet, the absorbent structure having a transverse axis dividing the absorbent structure into a front panel terminating in a front end region and a rear panel terminating in a rear end region, the absorbent structure being delimited by opposed longitudinal edges and opposed transverse edges, and a pair of opposed belt halves attached to the absorbent structure at the rear end region of the rear panel by a respective joint, each belt half extending about a second longitudinal axis such that each belt half extends outwardly from a respective longitudinal edge of the absorbent structure. The joint between each belt half and the absorbent structure is designed such that when each belt half is subjected to a tension force of 35 N acting along the second longitudinal axis and the second longitudinal axis creates an angle $\alpha$ to said transverse axis of said absorbent structure, the following minimum average release times (t) of each said belt half from said absorbent structure are attained:

when $\alpha=10°$, $t \geq 720$ seconds;
when $\alpha=20°$, $t \geq 330$ seconds;
when $\alpha=25°$, $t \geq 240$ seconds;
when $\alpha=30°$, $t \geq 180$ seconds; and
when $\alpha=40°$, $t \geq 75$ seconds.

In a preferred embodiment of the invention, the following minimum average release times (t) of each belt half from the absorbent structure are attained:
when $\alpha=10°$, $t \geq 740$ seconds;
when $\alpha=20°$, $t \geq 340$ seconds;
when $\alpha=25°$, $t \geq 245$ seconds;
when $\alpha=30°$, $t \geq 190$ seconds; and
when $\alpha=40°$, $t \geq 80$ seconds.

In a more preferred embodiment of the invention, the following minimum average release times (t) of each belt half from the absorbent structure are attained:
when $\alpha=10°$, $t \geq 760$ seconds;
when $\alpha=20°$, $t \geq 350$ seconds;
when $\alpha=25°$, $t \geq 250$ seconds;
when $\alpha=30°$, $t \geq 200$ seconds; and
when $\alpha=40°$, $t \geq 85$ seconds.

In a further embodiment of the invention, the following minimum average release times (t) of each belt half from the absorbent structure are attained:
when $\alpha=10°$, $t \geq 780$ seconds;
when $\alpha=20°$, $t \geq 360$ seconds;
when $\alpha=25°$, $t \geq 255$ seconds;
when $\alpha=30°$, $t \geq 210$ seconds; and
when $\alpha=40°$, $t \geq 90$ seconds.

In accordance with a most preferred embodiment of the invention, the following minimum average release times (t) of each belt half from the absorbent structure are attained:
when $\alpha=10°$, $t \geq 800$ seconds;
when $\alpha=20°$, $t \geq 370$ seconds;
when $\alpha=25°$, $t \geq 260$ seconds;
when $\alpha=30°$, $t \geq 220$ seconds; and
when $\alpha=40°$, $t \geq 100$ seconds.

Thus, in accordance with the invention, by ensuring that the joint between each belt half and the absorbent structure can withstand a force of 35 N at predetermined values of the angle $\alpha$ for a minimum average release time per chosen angle, it has been found in practice that failure of the belted absorbent article due to loosening of the belt halves does not occur, at least not during normal use.

BRIEF DESCRIPTION OF THE DRAWINGS

The invention will be described in the following in greater detail by way of example only and with reference to the attached drawings, in which.

DETAILED DESCRIPTION OF PREFERRED EMBODIMENTS

In the drawings, reference numeral 10 generally denotes a belted absorbent article according to the present invention. The expression "belted" implies that the article is provided with means which pass around at least a portion of the waist of a wearer when worn and which means meet to thereby secure the article around the waist of the wearer. In the present invention, these means are belt halves 12, 14. Preferably, the invention is to be practised on a disposable article. In this respect, the term "disposable" means any article which is not intended to be laundered and which is normally discarded once removed from the wearer.

In addition to the belt halves 12, 14, the belted absorbent article further comprises an absorbent structure 16 extending about a first longitudinal axis 18. Thus, when the article is being worn, the first longitudinal axis will generally bisect the wearer into a left hand side and a right hand side when viewed from above. The absorbent structure 16 includes a topsheet 20, a backsheet 22 and an absorbent batt 24 disposed between the topsheet and the backsheet. The specific components used to form the absorbent structure may be any of the types commonly used for such purposes. For example, a suitable topsheet 20 may be any soft flexible non-irritating liquid permeable material, such as woven or nonwoven webs of natural fibres (e.g. wood or cotton fibres), synthetic fibres (e.g. polyester or polypropylene fibres or coform fibres), combinations of natural and synthetic fibres, apertured films or porous foams. Preferably, the topsheet 20 is manufactured from a nonwoven spunbonded polypropylene material having a basis weight of less than 20 g/m$^2$. Nevertheless, when the topsheet comprises a nonwoven web, the nonwoven web may instead be carded, wet-laid, meltblown, hydroformed or hydroentangled. The backsheet 22 is impervious to liquids and is preferably manufactured from a thin plastic film such as polyethylene, polypropylene, polyvinyl-chloride, or the like, or composite materials such as a film coated nonwoven material. The absorbent core 24 may be made in widely varying sizes and shapes and may comprise any suitable wettable hydrophilic fibres such as cellulosic fibres, possibly blended with synthetic polyolefin fibres. In certain embodiments, the absorbent core 24 may comprise a mixture of superabsorbent hydrogel-forming particles mixed with the hydrophilic fibres.

The topsheet 20 and the backsheet 22 are connected together, either directly or indirectly, using any suitable known means. For example, the topsheet and the backsheet can be affixed directly to each other in selected areas using continuous or patterned layers of adhesive. The adhesive layer or layers may be sprayed or extruded in lines or dots.

Figure 2:
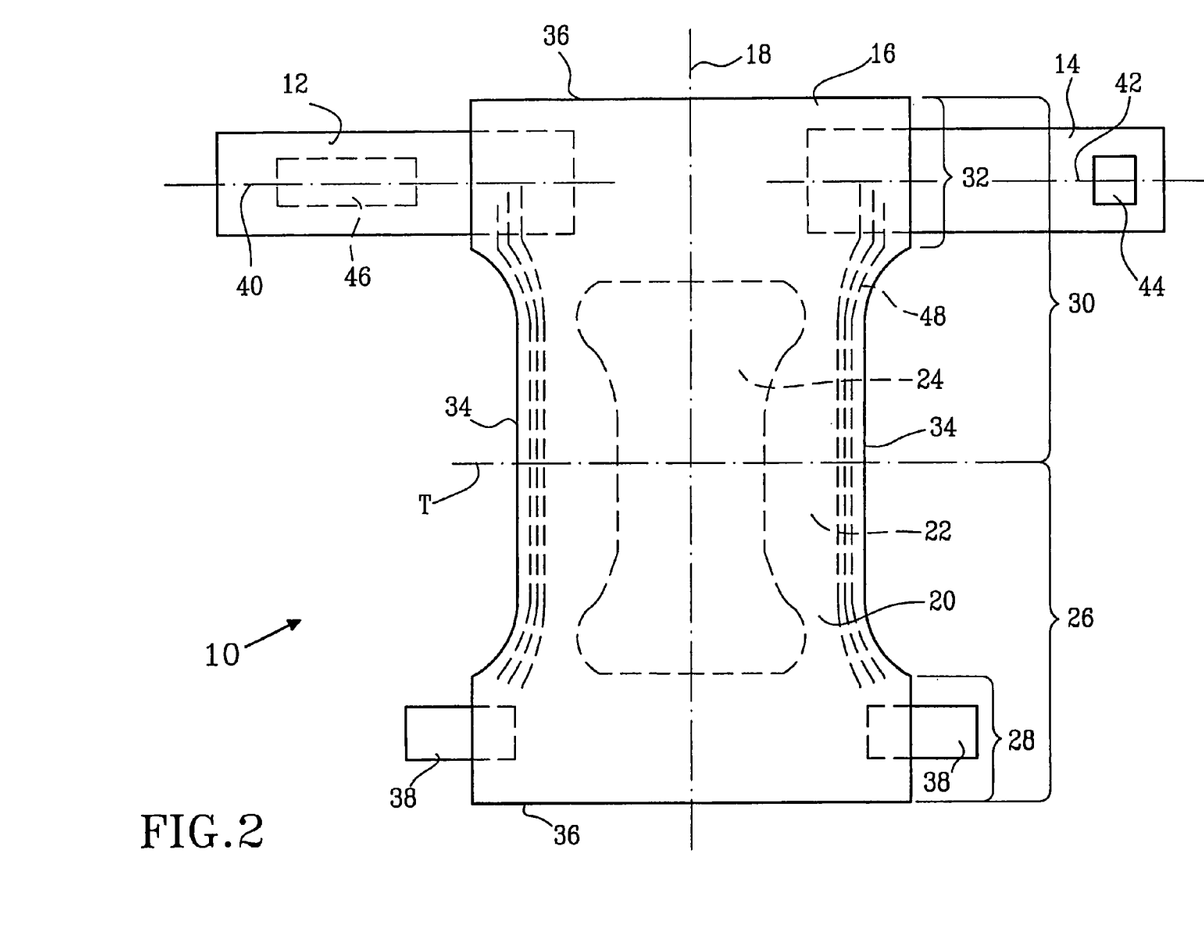
FIG. 2 is a schematic plan view of a belted absorbent article according to the present invention.

As is most clearly apparent from FIG. 2, the absorbent structure has a transverse axis T dividing the structure into a front panel 26 terminating in a front end region 28 and a rear panel 30 terminating in a rear end region 32. The absorbent structure is delimited by opposed longitudinal edges 34 and opposed transverse edges 36. Projecting from its opposed longitudinal edges 34, the front end region 28 displays fastening tabs 38. In a manner which will be explained in greater detail below, the fastening tabs 38 form part of a fastening system and are arranged to cooperate with corresponding parts of the fastening system on the belt halves 12, 14. Although the fastening tabs 38 are shown projecting from the longitudinal edges 34 of the front panel of the absorbent structure 16, it is to be understood that the tabs may instead project from the transverse edge 36. In a further alternative embodiment, the fastening tabs 38 may be in the form of one or more patches affixed to the topsheet 20 on the front panel 26.

Each belt half extends about a respective longitudinal axis (hereinafter referred to as the second longitudinal axis) 40, 42, with the belt halves being joined to the absorbent structure 16 such that the two belt halves 12, 14 extend generally perpendicularly with respect to the first longitudinal axis 18 of the absorbent structure 16. Accordingly, in the shown embodiment, the two belt halves 12, 14 extend generally perpendicularly from the longitudinal edges 34 at the rear end region 32 of the rear panel 30 of the absorbent structure 16. It is, however, to be understood that the belt halves may be manufactured such that they form an angle to either the first longitudinal axis 18 or to the longitudinal edges 34. The belt halves may be made of any suitable material or material combinations. In an exemplary embodiment, the belt halves are made from a laminate of an embossed transparent polypropylene film and a thermobonded nonwoven web of 30 g/m² basis weight. For improved wearer comfort, the belt halves are attached to the absorbent structure such that, when worn, the nonwoven web faces the wearer. In another embodiment, the belt halves may be made exclusively of nonwoven material. Depending on the intended size of the wearer, each belt half 12, 14 has a transverse extension of typically 10 to 12 cm and a longitudinal extension (i.e. the extension beyond the longitudinal edge 34 of the absorbent structure) of, for example, 35 cm. The belt halves are preferably identical, though it is to be understood that the absorbent article of the present invention may also have belt halves or different length and/or width.

The inside surface, i.e. that surface of the belt half facing the wearer when worn, of one belt half (belt half 14 in FIG. 2) is provided with a first fastening means 44 for releasable engagement with a complementary second fastening means 46 on the outer surface of the other belt half 12 to thereby allow the belt to be secured around the waist of the wearer. The actual type of belt fastening means may be any of those known in the art, for example a hook-and loop system, an adhesive system, a system of buttons and button-holes, etc. Irrespective of the type of fastening system employed, the fastening system should be capable of allowing adjustment of the tension of the belt halves around the waist of the wearer. Thus, in the embodiment shown on FIG. 2, the first fastening means is a patch of hook material while the second fastening means is a strip of loop material extending over a significant length of the belt half 12. It will of course be apparent to the skilled person that more than one patch of hook material may be used and that the strip of loop material may be a plurality of smaller patches of loop material.

The surface of the belt halves remote from the wearer when worn, i.e., the outer surface of the belt halves, is provided with means (not shown) forming a part of the fastening system of the absorbent article. The means on the belt halves is complementary to, and therefore dependent on, the type of fastening tab 38 employed in the front end region 28 of the front panel 26. Thus, if the fastening tabs 38 are adhesive tabs, at least a region of the outer surface of the belt halves 12, 14 should be capable of releasable engagement of the adhesive tabs. In the case in which the outer surface of the belt halves is a plastics film, it is advantageous to provide a reinforced so-called landing zone or zones for the tabs to engage with. If the fastening tabs 38 are hook tabs of a hook-and-loop fastening system, the outer surface of the belt halves will be provided with, or made from, a loop material for engagement with the hook fastening tabs. Another possibility is that the outer surface of the belt halves is provided with patches of hook material for engagement with loop material of the topsheet 20 or patches of loop material attached to the topsheet in the front end region 28 of the front panel 26.

In a manner known per se in the art, the absorbent article of the present invention may be provided with elasticated leg cuffs to thereby provide improved sealing of the article around the legs of the wearer when worn. As is most clearly shown in FIGS. 2 and 3, the absorbent structure 16 is provided with elastic ribbons 48 or strands affixed between the topsheet 20 and the backsheet 22. The elastic ribbons extend from an area in the rear end region 32 remote from the transverse edge 36 along a path generally parallel to the longitudinal edges 34 of the absorbent structure to an area in the front end region 28 remote from its transverse edge 36. In the illustrated embodiment, three elastic ribbons 48 or strands are shown for each leg cuff. The person skilled in the art will, however, appreciate that the actual number of elastic ribbons may be varied, as may their size. Thus, although the ribbons are illustrated as threads, it will be appreciated that strips of elastic material may be used instead.

Figure 3:
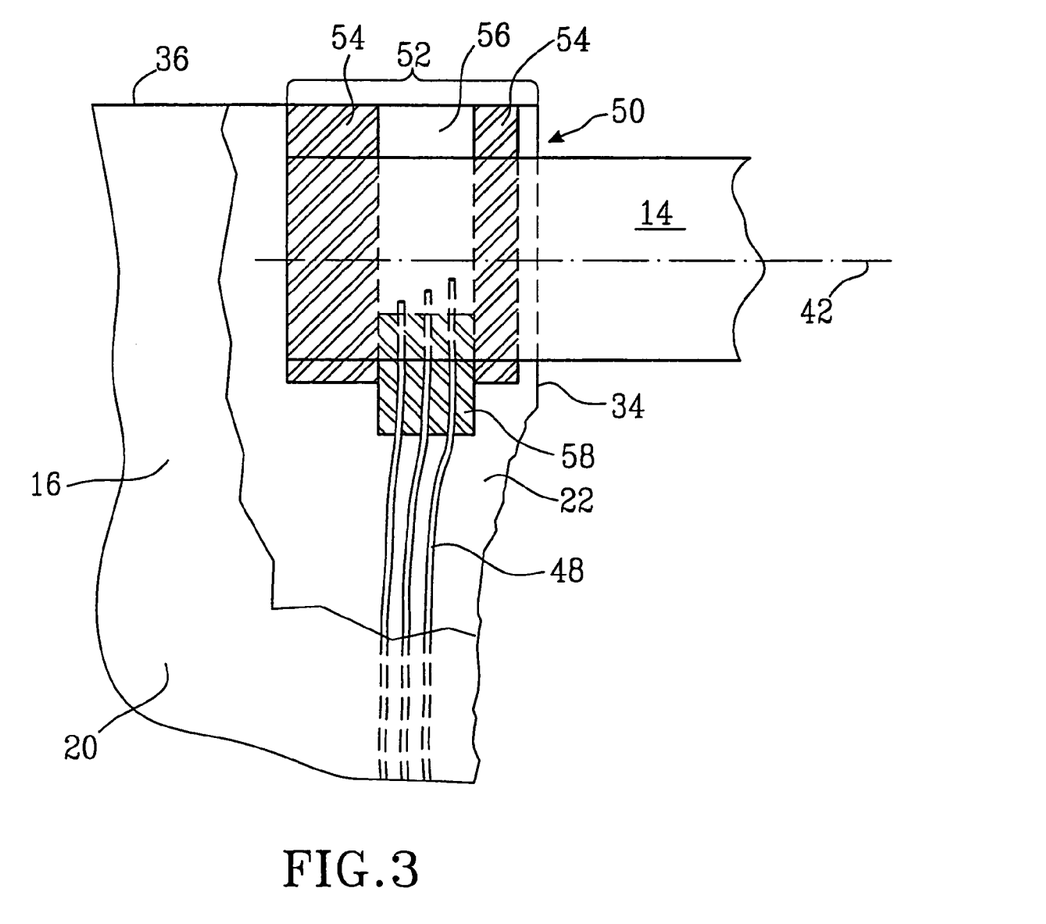
FIG. 3 is an enlarged view of the joint between a belt half and the absorbent structure of the belted absorbent article according to the present invention.

Each belt half 12, 14 is attached to the absorbent structure 16 at the rear end region 32 of the rear panel 30 by a respective joint, generally denoted by reference numeral 50. One example of a joint 50 which may be used in the absorbent article of the present invention is illustrated in FIG. 3. It is to be understood that, although the joint will be described below only with reference to one belt half 14, an identical joint may be used for the other belt half 12. A length 52 of the belt half 14 is attached to the absorbent structure 16 at the rear end region 32 between the topsheet 20 and the backsheet 22. The length 52 of the belt half thus sandwiched between the topsheet and backsheet will vary depending on the size of the absorbent article, but is typically between 8 and 10 cm. When, and in what order, the belt half is attached to the topsheet and backsheet will depend on the chosen manufacturing process. The belt half 14 is generally spaced a short distance, for example about 1 cm, from the transverse edge 36 of the absorbent structure and, prior to being worn, the longitudinal axis 42 of the belt half may extend substantially parallel to the transverse edge. Thus, in the illustrated embodiment, the longitudinal axis of the belt half extends parallel to the transverse axis T of the absorbent structure. The joint 50 between the belt half 14 and the rear end region 32 comprises two spaced substantially parallel lines of attachment 54 between the belt half and the backsheet 22. The line of attachment 54 adjacent the longitudinal edge 34 of the absorbent structure 16 may be spaced a short distance from the longitudinal edge. This line of attachment is generally narrower than the line of attachment remote from the longitudinal edge 34 of the absorbent structure. The two spaced lines of attachment 54 generally extend from the transverse edge 36 of the rear end region parallel to the longitudinal axis 18 of the absorbent structure across the entire width of the belt half and slightly beyond. Although the lines are shown to be continuous, it is to be understood that they may instead comprise intermittent lines of attachment. Preferably, the lines of attachment 54 are adhesive bond lines, though any attachment methods, such as thermal or ultrasonic bonding, may be employed.

The two spaced substantially parallel lines of attachment 54 at least partially delimit a non-attached longitudinally extending region 56 between the belt half 14 and the backsheet 22. This non-attached region 56 permits the elastic ribbons 48 or strands of the elasticised leg cuffs to snap back during manufacture. Thus, free ends of the elastic ribbons 48 or strands reside in the non-attached longitudinally extending region 56. To firmly anchor the elastic ribbons 48 within the absorbent structure 16, the joint 50 between the belt half 14 and the rear end region 32 further comprises a region 58 of attachment between the backsheet 22 and the belt half. The region 58 of attachment extends between the two spaced substantially parallel lines of attachment 54 over the elastic ribbons 48. Advantageously, the region 58 of attachment extends in the longitudinal direction beyond the point at which the two spaced parallel lines of attachment 54 terminate. The joint 50 between the belt half 14 and the rear end region 32 may further comprise at least one region of bonding between the belt half and the topsheet 20. Such region may comprise substantially the entire surface of the belt half which lies adjacent the topsheet 20. This region of bonding may be suitably achieved by spray bonding the topsheet to the belt half.

Figure 4:
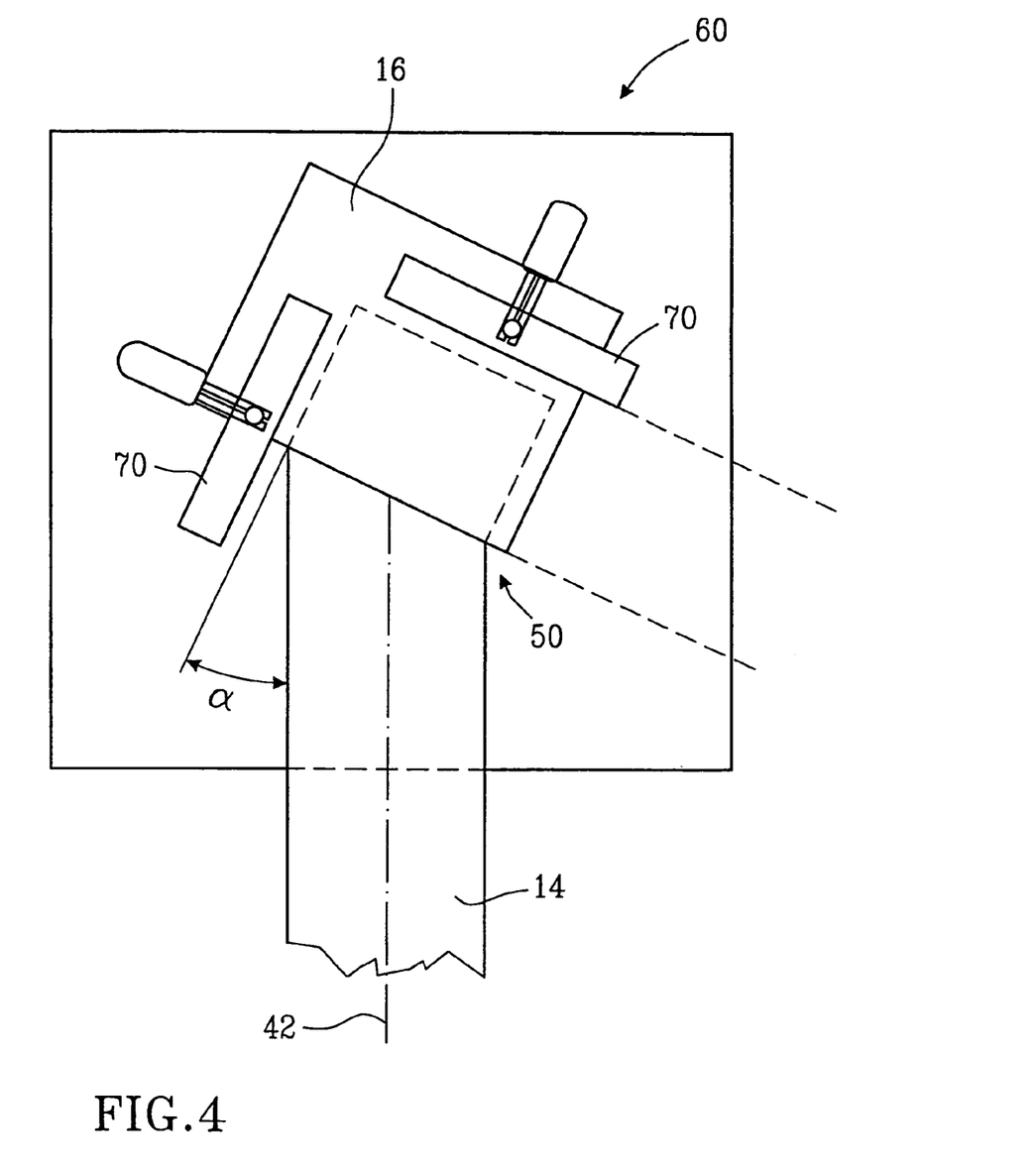
FIG. 4 is a schematic view of a cut out section of the article according to the present invention being subjected to a test procedure.

In accordance with the present invention, the joint 50 is designed to meet certain minimum requirements. The present inventors have discovered that, for the absorbent article to function satisfactorily, the joint 50 should be capable of withstanding a certain tension force applied to the belt halves at a certain angle α to the transverse axis of the absorbent structure for a certain minimum period of time. Thus, and in a manner which will be explained in greater detail below, the joint is subjected to a test procedure such that, and as illustrated in FIG. 4, a portion of the absorbent structure 16 is secured to a test rig, generally denoted reference numeral 60, and a load of 35 N is applied to the belt half 14 while the belt half external of the absorbent structure 16 is maintained at a predetermined angle α to the transverse axis of the absorbent structure. The time up to failure of the joint, i.e. when the belt half completely dissociates from the absorbent structure, is measured. The time to failure is hereinafter referred to as the release time of the joint. In accordance with the present invention, the minimum average release times of the joint should be:
   when α=10°, t≧720 seconds;
   when α=20°, t≧330 seconds;
   when α=25°, t≧240 seconds;
   when α=30°, t≧180 seconds; and
   when α=40°, t≧75 seconds.

In a preferred embodiment of the invention, the following minimum average release times (t) of each belt half from the absorbent structure are attained:
   when α=10°, t≧740 seconds;
   when α=20°, t≧340 seconds;
   when α=25°, t≧245 seconds;
   when α=30°, t≧190 seconds; and
   when α=40°, t≧80 seconds.

In a more preferred embodiment of the invention, the following minimum average release times (t) of each belt half from the absorbent structure are attained:
   when α=10°, t≧760 seconds;
   when α=20°, t≧350 seconds;
   when α=25°, t≧250 seconds;
   when α=30°, t≧200 seconds; and
   when α=40°, t≧85 seconds.

In a further embodiment of the invention, the following minimum average release times (t) of each belt half from the absorbent structure are attained:
   when α=10°, t≧780 seconds;
   when α=20°, t≧360 seconds;
   when α=25°, t≧255 seconds;
   when α=30°, t≧210 seconds; and
   when α=40°, t≧90 seconds.

In accordance with a most preferred embodiment of the invention, the following minimum average release times (t) of each belt half from the absorbent structure are attained:
   when α=10°, t≧800 seconds;
   when α=20°, t≧370 seconds;
   when α=25°, t≧260 seconds;
   when α=30°, t≧220 seconds; and
   when α=40°, t≧100 seconds.

The minimum average release times are established in the following manner.

Figure 5:
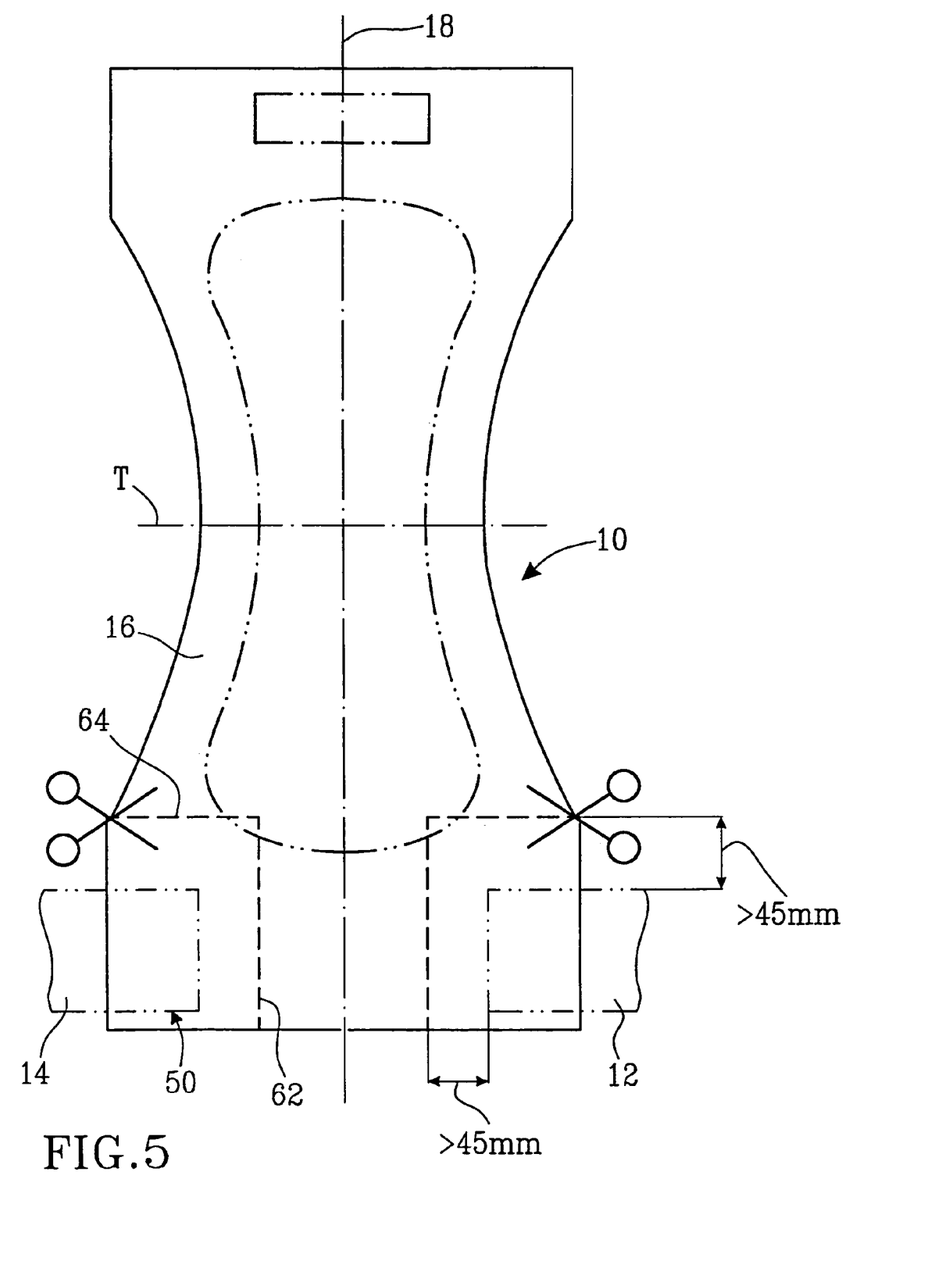
FIG. 5 is a schematic plan view illustrating sections of the belted absorbent article according to the present invention which are to be cut out and tested.

With reference to FIG. 5, a section of the rear panel 30 including the joint 50 is cut out from the absorbent structure 16. A first cut line 62 is made parallel to the longitudinal axis 18 of the absorbent article at least 45 mm from the end edge of the belt half 14 nearest the longitudinal axis 18. The first cut line 62 extends beyond the lower edge, i.e. the edge nearest the transverse axis T of the absorbent article, of the belt half 14 by at least 45 mm. The first cut line intersects a second cut line 64 extending parallel to the transverse axis T of the absorbent article at least 45 mm from the lower edge of the belt half 14. The thus cut out section of the absorbent structure 16 including the joint 50 is then clamped in the test rig 60 which will be described in greater detail in the following.

Figure 6:
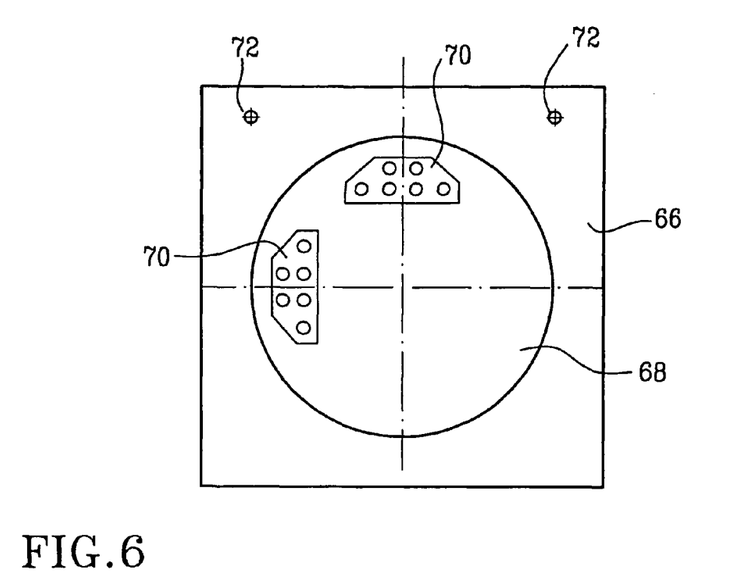
FIG. 6 is a schematic elevational view of a test rig for subjecting cut out sections of the belted absorbent product to a test procedure.
Figure 7:
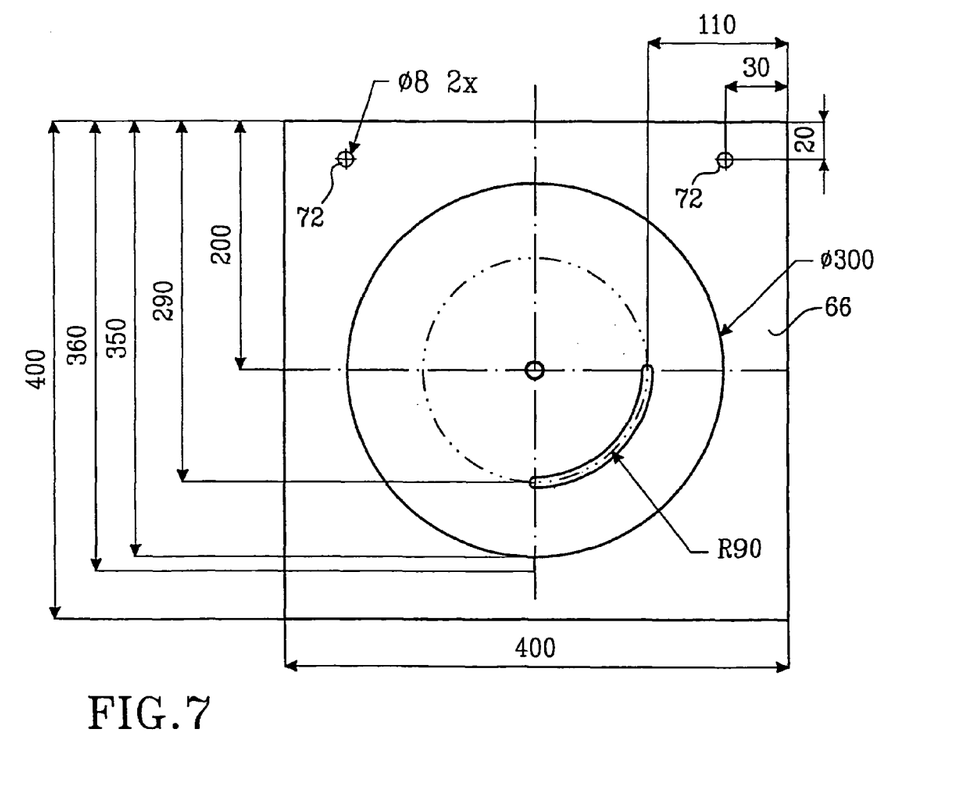
FIG. 7 is an engineering drawing in the form of an elevational view of one component of the test rig of FIG. 6.
Figure 8:
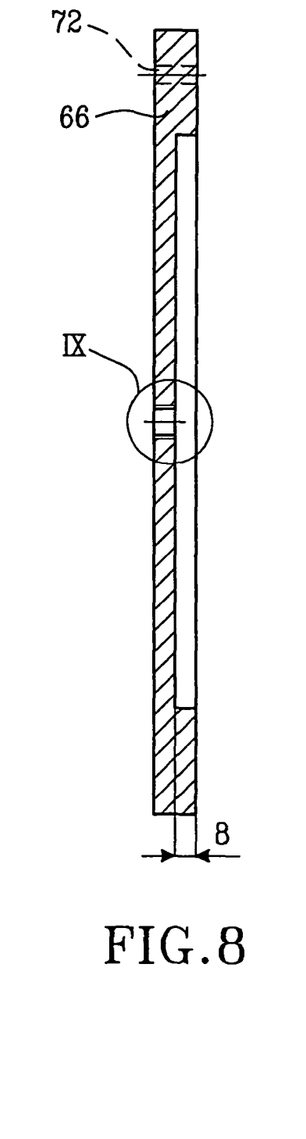
FIG. 8 is an engineering drawing in the form of an end view of the component of FIG. 7.
Figure 9:
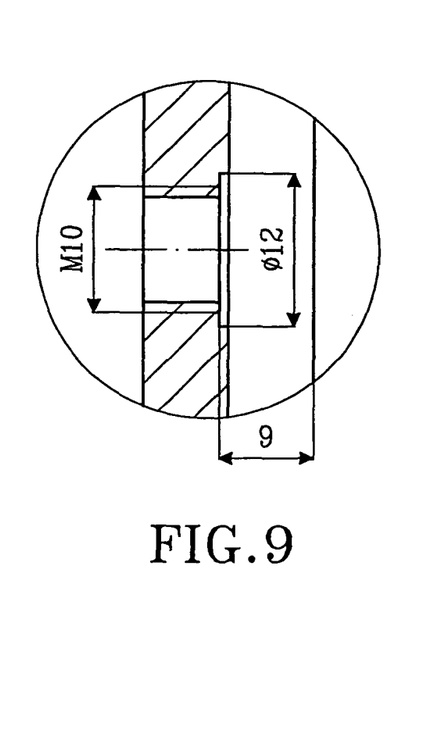
FIG. 9 is an enlarged view of a portion of the component of FIG. 8.
Figure 10:
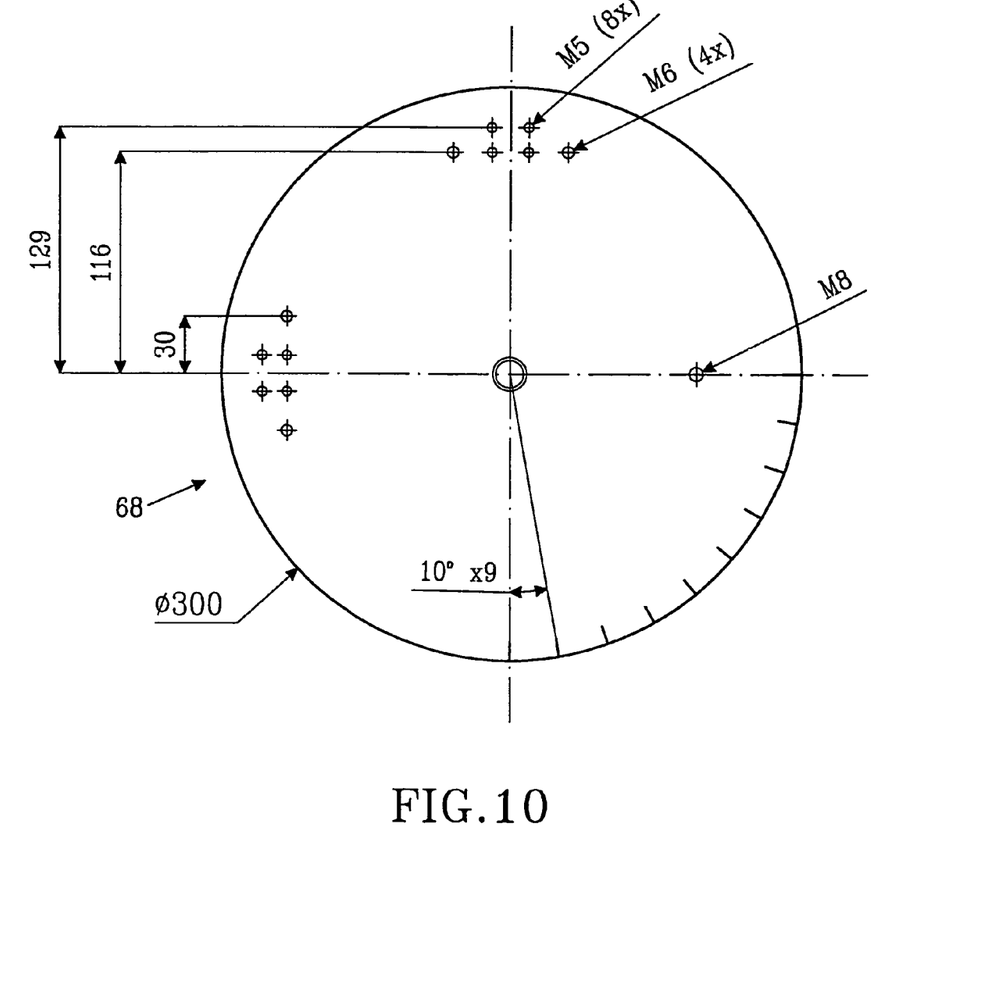
FIG. 10 is an engineering drawing in the form of an elevational view of a second component of the test rig of FIG. 6.
Figure 11:
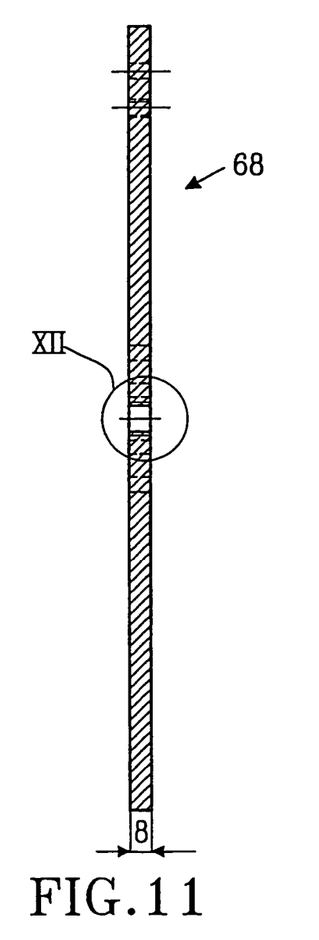
FIG. 11 is an engineering drawing in the form of an end view of the component of FIG. 10.
Figure 12:
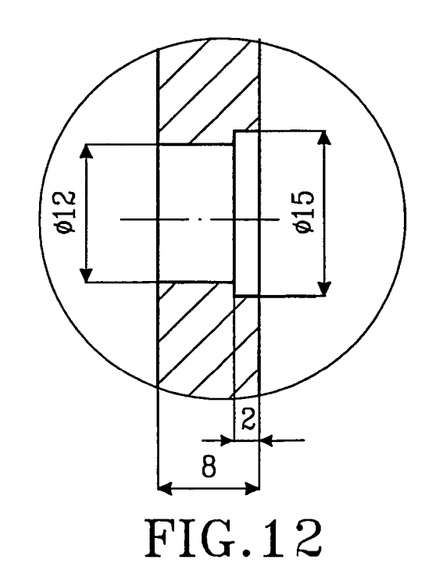
FIG. 12 is an enlarged view of a portion of the component of FIG. 11.
Figure 13:
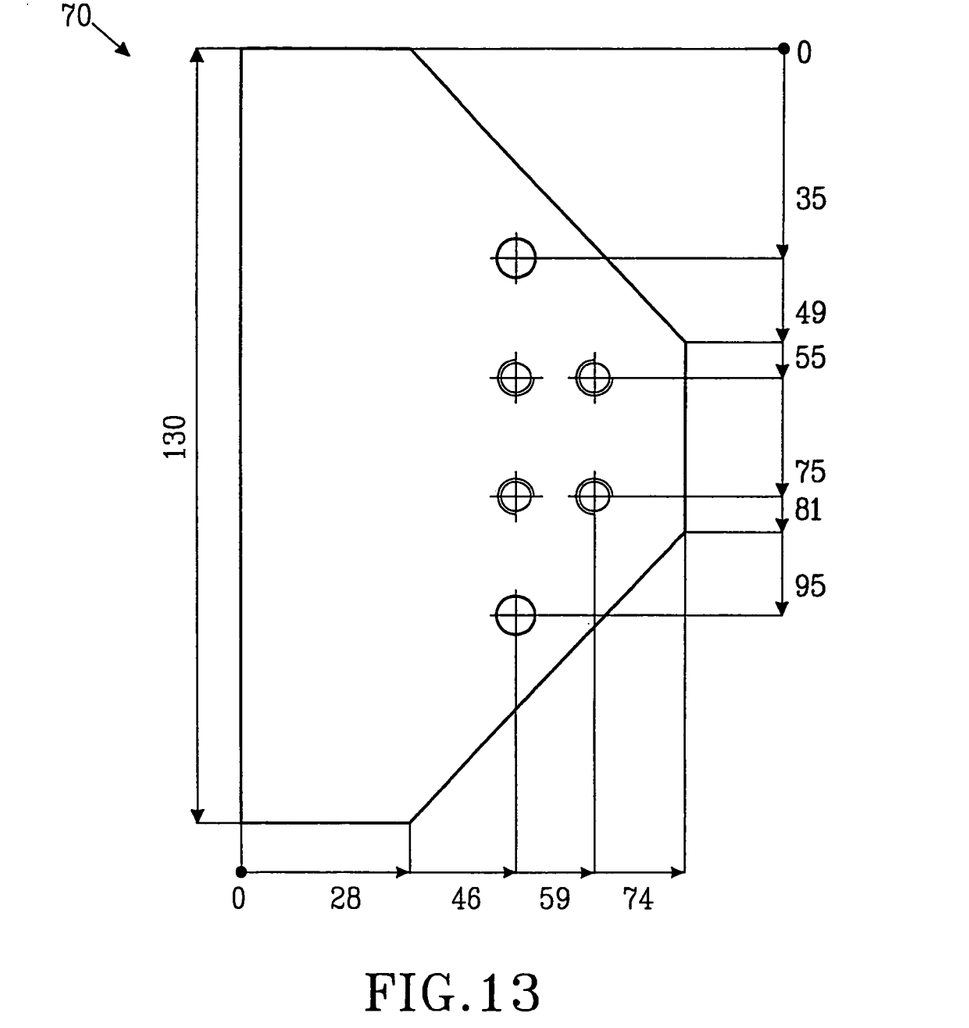
FIG. 13 is an engineering drawing in the form of an elevational view of a third component of the test rig of FIG. 6.
Figure 14:
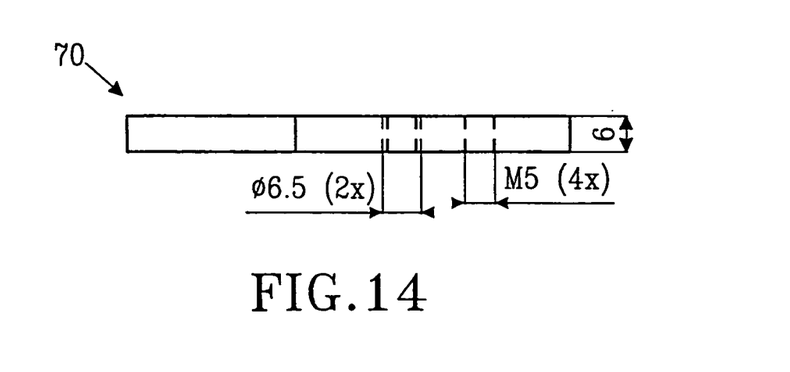
FIG. 14 is an engineering drawing in the form of an end view of the component of FIG. 13.

With reference to FIG. 6, the test rig 60 comprises a rectangular base plate 66 to which a rotatable plate 68 is mounted. A pair of clamps 70 spaced at 90° to each other are mounted on the rotatable plate 68. With reference to FIG. 4, the rotatable plate 68 can be rotated with respect to the rectangular base plate 66 such that suitable values of the angle α are obtainable. The test rig 60 is provided with locking means to enable the rotatable plate to be locked at angular positions at which desired values of α are obtained. The rectangular base plate 66 may be provided with holes 72 to enable the base plate to be maintained in a vertical position on a frame (not shown) or the like.

Dimensions and constructional details of the test rig 60 will be apparent from the attached FIGS. 7 to 14.

The method for establishing the minimum average release times is the following.

Sections are cut out from fifty identical absorbent articles. In order to avoid the influence of aging of the articles on the test results, the articles should be no more than 6 months old, i.e., the test is to be performed on articles which have been manufactured during the past six months. The cut out section of a first absorbent structure 16 is secured by the clamps 70 to the test rig 60, as shown in FIG. 4. The orientation of the cut out section must be such that the clamps 70 clamp the cut out section along lines parallel to the transverse axis T and the longitudinal axis 18 of the absorbent article. In FIG. 4, the edges of the belt half 14 within the absorbent structure 16 are parallel to the transverse and longitudinal axes respectively. Thus, these edges are parallel to, and spaced from the clamps 70. In order to ensure that the clamps do not contact the belt half 14, a spacing of about 1 cm may be employed. The rectangular base plate 66 is held vertically and the rotatable plate 68 is rotated until an angle α of 10° is attained. The rotatable plate is locked at this position and a weight is clamped to the free end of the belt half 14. The weight is slowly released until it applies a tension to the belt half. The weight is then allowed to hang freely. The weight and clamp together apply a force of 35 N to the belt half. As soon as the weight is allowed to hang freely, a stop watch is started. As soon as the belt half completely dissociates from the absorbent structure, i.e., when the weight hits the floor, the stop watch is stopped and the elapsed time is noted.

The above procedure is repeated for nine further cut out sections at α=10°.

For the next ten cut out sections, the above procedure is repeated for α=20°.

Batches of ten cut out sections are then subjected to the above procedure, but for α=25°, 30° and 40°.

EXAMPLE

The above procedure was conducted on a belted absorbent article to ensure that its joint 50 between each belt half and the absorbent structure is sufficiently strong. The following results were obtained (note that the elapsed time is given in minutes and seconds):

|  | α = | | | | |
| --- | --- | --- | --- | --- | --- |
|  | 10° | 20° | 25° | 30° | 40° |
| Sample 1 | 12:31 | 05:35 | 03:21 | 04:23 | 01:49 |
| 2 | 10:16 | 05:42 | 05:51 | 04:14 | 01:52 |
| 3 | 12:52 | 06:27 | 04:41 | 03:25 | 01:25 |
| 4 | 13:34 | 07:10 | 03:37 | 02:58 | 01:17 |
| 5 | 11:05 | 05:43 | 04:28 | 02:59 | 01:45 |
| 6 | 11:45 | 05:21 | 04:01 | 03:29 | 00:52 |
| 7 | 16:24 | 07:11 | 03:59 | 02:18 | 01:25 |
| 8 | 12:07 | 05:00 | 04:39 | 02:39 | 01:09 |
| 9 | 11:27 | 04:57 | 03:27 | 03:36 | 00:46 |
| 10 | 11:34 | 04:15 | 03:28 | 03:36 | 01:19 |
| Average: | 12:21 | 05:44 | 04:09 | 03:21 | 01:21 |
| St. dev | .01:41 | 00:57 | 00:46 | 00:39 | 00:22 |
| Min | 10:16 | 04:15 | 03:21 | 02:18 | 00:46 |
| Max | 16:24 | 07:11 | 05:51 | 04:23 | 01:52 |

Thus, the average release times for the joint of the EXAMPLE are:
when α=10°, t=741 seconds;
when α=20°, t=344 seconds;
when α=25°, t=249 seconds;
when α=30°, t=201 seconds;
when α=40°, t=81 seconds.

The above EXAMPLE relates to a belted absorbent article in which the belt halves are substantially rectilinear, i.e., the upper and lower longitudinal edges of the belt halves are substantially parallel to the second longitudinal axis 42. Thus, the angle α may be determined either by measuring the angle as shown in FIG. 4, or by measuring the angle subtended by the second longitudinal axis 42. In cases in which the belt halves are non-rectilinear, i.e., the belt halves are curved, the angle α is determined by hanging the load of 35 N from the remote end of the belt half such that the load acts along the longitudinal axis of the belt half and determining the midpoint of the belt half between its upper and lower longitudinal edges at the joint 50. A vertical line will thus be attained between the mid point and the load. The angle that this vertical line subtends to the transverse axis T of the absorbent article corresponds to the angle α.

The invention is not restricted to the embodiments described above and shown in the drawings, but may be varied within the scope of the appended claims. For example, the topsheet 20 of the absorbent structure 16 may be provided with so-called standing gathers to assist in retaining bodily wastes within the confines of the absorbent structure.

What is claimed is:

1. A belted absorbent article comprising: an absorbent structure extending about a first longitudinal axis, said absorbent structure including a topsheet, a backsheet and an absorbent batt disposed between said topsheet and said backsheet, said absorbent structure having a transverse axis dividing the absorbent structure into a front panel terminating in a front end region and a rear panel terminating in a rear end region, said absorbent structure being delimited by opposed longitudinal edges and opposed transverse edges, and a pair of opposed belt halves attached to said absorbent structure at said rear end region of said rear panel, each of said belt halves being attached by a respective joint, each belt half extending about a longitudinal axis of the belt such that each belt half extends outwardly from a respective longitudinal edge of the absorbent structure, wherein each of said joints between each said belt half and said absorbent structure is designed such that when each said belt half is subjected to a tension force of 35 N acting along said longitudinal axis of the belt and said longitudinal axis of the belt creates an angle (.alpha.) to said transverse axis of said absorbent structure, the following minimum average release times (t) of each said belt half from said absorbent structure are attained:
when α=10°, t≧720 seconds;
when α=20°, t≧330 seconds;
when α=25°, t≧240 seconds;
when α=30°, t≧180 seconds; and
when α=40°, t≧75 seconds; wherein each said belt half is attached to said absorbent structure at said rear end region between said topsheet and said backsheet.

2. The article as claimed in claim 1, wherein said two spaced substantially parallel lines of attachment at least partially delimit a non-attached longitudinally extending region between each said belt half and said backsheet within which region ends of elastic ribbons forming elasticised leg cuffs reside.

3. The article as claimed in claim 2, wherein each of said joints between each said belt half and said rear end region further comprises a region of attachment between said backsheet and each said belt half, said region of attachment extending between said two spaced substantially parallel lines of attachment over said elastic ribbons.

4. The article as claimed in claim 3, wherein each of said joints between each said belt half and said rear end region further comprises at least one region of bonding between each said belt half and said topsheet.

5. The article as claimed in claim 1, wherein each of said belt halves is attached to the absorbent structure between said topsheet and said backsheet, and each of said joints includes a region of attachment between the respective belt half and said backsheet and a region of attachment between the respective belt half and said topsheet.

6. The article as claimed in claim 5, wherein the region of attachment between the respective belt half and said backsheet includes first and second spaced substantially parallel lines of attachment between each respective belt half and said backsheet.

7. A belted absorbent article comprising:
an absorbent structure extending about a first longitudinal axis, said absorbent structure including a topsheet, a backsheet and an absorbent batt disposed between said topsheet and said backsheet, said absorbent structure having a transverse axis dividing the absorbent structure into a front panel terminating in a front end region and a rear panel terminating in a rear end region, said absorbent structure being delimited by opposed longitudinal edges and opposed transverse edges, and a pair of opposed belt halves comprising nonwoven material attached to said absorbent structure at said rear end region of said rear panel, each of said belt halves being attached by a respective joint, each belt half extending about a longitudinal axis of the belt such that each belt half extends outwardly from a respective longitudinal edge of the absorbent structure, wherein each of said belt halves is attached to the absorbent structure between said topsheet and said backsheet with the respective joints each comprising at least one region of bonding between each said belt half and said topsheet, and each of said joints is spaced from the longitudinal edge associated with the respective belt half;

wherein each of said joints between each said belt half and said absorbent structure is such that when each said belt half is subjected to a tension force of 35 N acting along said longitudinal axis of the belt, and said longitudinal axis of the belt creates an angle ($\alpha$) to said transverse axis of said absorbent structure, the following minimum average release times (t) of each said belt half from said absorbent structure are attained:

when $\alpha=10°$, $t \geqq 720$ seconds;
when $\alpha=20°$, $t \geqq 330$ seconds;
when $\alpha=25°$, $t \geqq 240$ seconds;
when $\alpha=30°$, $t \geqq 180$ seconds; and
when $\alpha=40°$, $t \geqq 75$ seconds.

\* \* \* \* \*